United States Patent [19]
Gerits et al.

[11] Patent Number: 5,661,234
[45] Date of Patent: Aug. 26, 1997

[54] APPARATUS FOR MEASURING SURFACE TENSION

[75] Inventors: Erik Jan Mathijs Gerits, Genk; Willy Van Der Perre, Brasschaat, both of Belgium

[73] Assignee: Heraeus Electro-Nite International N.V., Houthalen, Belgium

[21] Appl. No.: 496,073

[22] Filed: Jun. 28, 1995

[30] Foreign Application Priority Data

Jul. 8, 1994 [DE] Germany ............... 44 23 720.0

[51] Int. Cl.$^6$ ................... G01N 13/02
[52] U.S. Cl. ................... 73/64.48
[58] Field of Search ............. 73/54.15, 54.21, 73/64.48, 64.51, 64.52

[56] References Cited

U.S. PATENT DOCUMENTS

| | | | |
|---|---|---|---|
| 3,765,227 | 10/1973 | Campbell et al. | 73/64.51 |
| 3,780,568 | 12/1973 | Goldmann et al. | 73/64.51 |
| 4,527,421 | 7/1985 | Miller, Jr. | 73/64.51 |

FOREIGN PATENT DOCUMENTS

| | | |
|---|---|---|
| 0149500 | 7/1985 | European Pat. Off. . |
| 1 341 670 | 9/1963 | France . |
| 2 393 610 | 5/1979 | France . |
| 2231598 | 2/1973 | Germany . |
| 26 35 373 | 4/1977 | Germany . |
| 2915956 | 11/1980 | Germany . |
| 4228942 | 1/1994 | Germany . |
| 0532789 | 10/1976 | U.S.S.R. ............... 73/64.51 |
| 0783654 | 11/1980 | U.S.S.R. ............... 73/64.51 |

OTHER PUBLICATIONS

W.L. Falke, A.E. Schwaneke, and R. W. Nash, "Surface Tension of Zinc: The Positive Temperature Coefficient", Metallurgical Transactions B, vol. 8B, pp. 301–303, Jun. 1977.

E. Selcuk and D.H. Kirkwood, "Surface Energies Of Liquid Cast Irons Containing Magnesium and Cerium", *Journal of The Iron and Steel Institute*, pp. 134–140, Feb. 1973.

G.A. Irons and R.I.L. Guthrie, "Bubble Formation at Nozzles in Pig Iron", *Metallurgical Transactions B*, vol. 9B, pp. 101–110, Mar. 1978.

Goldmann et al., "Measurement of solder–flux–vapor surface tension by a modified maximum bubble presure technique", Review of Scientific Instruments, vol. 47, No. 3, pp. 324–325, Mar. 1976.

*Primary Examiner*—Michael Brock
*Attorney, Agent, or Firm*—Panitch Schwarze Jacobs & Nadel, P.C.

[57] ABSTRACT

An apparatus for the measurement of the surface tension of liquids by means of a capillary tube for supplying gas, the tube having a connector and a nozzle, may be used in a measuring device. In order to create an apparatus that is easy to manufacture and handle, and that can be used reliably in a variety of liquids, the capillary tube is arranged, at least partially, in a crucible for receiving the liquid and is mounted on the wall of the crucible, whereby the connector is arranged outside the interior of the crucible. The connector is connected to the gas line of the measuring device and to a pressure sensor and/or a flow meter.

9 Claims, 8 Drawing Sheets

APPARATUS FOR MEASURING SURFACE TENSION

FIELD OF THE INVENTION

The invention pertains to an apparatus for measurement of the surface tension of liquids by means of a capillary tube for supplying gas, which has a connector and a nozzle, wherein the capillary tube is at least partially arranged in a crucible for receiving the liquid and wherein the connector is arranged outside the interior of the crucible. The invention also pertains to a measuring device with an apparatus of this type.

BACKGROUND OF THE INVENTION

An apparatus of this type is known from DE 22 31 598/A1, in which an apparatus and process are disclosed for determining the surface tension at the interface between liquids and gases. The apparatus uses a capillary tube for supplying gas with a connector and a nozzle. The capillary tube extends from above down into the container which receives the liquid. For measurement in molten metals the capillary tube is exposed to the heat which rises from the liquid to be measured. The capillary tube is mounted outside of the crucible. Such an arrangement is rather expensive.

A further apparatus of this type is known from DE 29 15 956/A1, in which is described an apparatus for measuring the surface tension of electrically conductive liquids. This apparatus has a capillary tube with a connecting sleeve and a nozzle. The end of the capillary tube that carries the nozzle is bent in a U-shape. The capillary tube is immersed from above in a liquid so that the nozzle is pointing in an upward direction. During operation of the apparatus, gas bubbles exit the nozzle and rise vertically inside a measuring tube. Two electrodes supplied with a voltage and connected to a time-keeping device are arranged on the measuring tube. When the gas bubbles pass between the electrodes, an interruption in the current flowing between the electrodes is brought about; the frequency of the interruptions that the gas bubbles cause in the electrical circuit is measured. The capillary tube is supplied with a flow of gas at a constant pressure, so that by making use of the frequency of the gas bubbles, the surface tension of the liquid can be determined.

Apparatus of this type are relatively complicated, since the capillary tube immersed in the liquid from above must be additionally mounted, like the measuring tube that has the electrodes. In conjunction with that, these elements must at the same time be protected from the increasing heat from molten metals, for example. Even the necessity for generating a flow of current within the liquid requires a relatively high expenditure for operation and safety. The danger of possible leaking currents also has to be viewed as a problem, if the gas bubbles do not perfectly insulate the electrodes from one another, since the results of the measurement can be distorted as a result of such current leaks.

Further, an apparatus is known from DE 42 28 942/C1 for measurement of the surface tension in liquids, wherein a capillary tube is partially arranged in a crucible for receiving the liquid, and wherein the capillary tube extends through the wall of the crucible. The gas to be conducted into the liquid flows through the capillary tube by way of a gas distribution unit. The gas flows out over the entire surface of the gas distribution unit, more or less irregularly, and thereby reaches the surface of the liquid under constantly changing conditions, where a sampling device catches a portion of the gas bubbles (as a rule the largest) and leads these as a measuring impulse to an analysis. Due to the different outlet openings, the different paths of the gas bubbles to the liquid, and due to the different size gas bubbles emitted by the distributing unit, as well as due to the inexactness of the receiving of the sampling device arranged over the liquid, an exact measurement of the surface tension with the described apparatus is not possible, since such an apparatus as a rule will not completely and correctly catch the gas bubbles which escape from the liquid at different places and in different sizes.

An additional apparatus for measurement of surface tensions is described in EP 0 149 500. Also, the determination of the frequency of gas bubbles, here in liquid pig iron, is described in G. A. Irons and R. I. C. Guthrie "Bubble Formation at Nozzles in Pig Iron," *Metallurgical Transactions B*, Volume 9B, pages 101–110, March 1978. Shown here is an apparatus in which the gas bubbles are detected by means of a microphone.

By making use of the surface tension, apparatus of this type are used, by way of example, to determine the properties of molten metals. Knowledge of the surface tension of molten cast iron makes it possible, among other things, to draw conclusions concerning the graphite morphology of the carbon contained in the cast iron, since the surface tension and the interfacial energy between various phases influence the microstructure of an alloy. This effect is described in the article by E. Selcuk and D. H. Kirkwood, "Surface Energies of Liquid Cast Irons Containing Magnesium and Cerium", *Journal of the Iron and Steel Institute*, pages 134–140, February 1973. Admixtures of cerium and magnesium with cast iron accelerate the formation of spheroidal graphite, that is, with increasing content of cerium or magnesium, the form of the graphite crystals changes from the lamellar type of graphite at the beginning to the spheroidal type (spheroidal graphite), which is sought in the practice of casting, because a graphite morphology of this type generates optimal strength properties in the cast iron.

SUMMARY OF THE INVENTION

Building on the present state of the art described above, it is an object of the present invention to create an apparatus that is easy to manufacture and handle, and that can be used reliably in a variety of liquids. For an apparatus of the above type, this object is achieved by means of the capillary tube being arranged, at least partially, in a crucible for receiving and holding the liquid and being mounted on a wall of the crucible, whereby the connector is arranged outside the interior of the crucible. An apparatus of this type is relatively simple to manufacture and ensures a secure placement of the capillary tube within the liquid with which the crucible is to be filled, without the danger that heat rising from a liquid that might be very hot, such as molten metals, could damage the mount or the measurement device, since no delicate parts need be placed above the liquid. An apparatus of this type is suitable for measuring the surface tensions of a variety of liquids, even for measurements in liquid cast iron in order to determine, among other things, the graphite morphology; for the determination of the sulphur content of pig iron; or in order to assess the modification treatment of aluminum-silicon alloys.

It is beneficial that the capillary tube be run through the wall of the crucible, particularly through the bottom of the crucible, in order to ensure a secure mounting. When it is arranged in the bottom, the capillary tube can be aligned vertically so that the gas bubbles can exit the capillary tube unrestrictedly and in accordance with their buoyancy.

Additionally, it is beneficial if the connector is mounted on or in the bottom of the crucible and is configured as a crucible mounting, since the crucible can then be placed with the connector directly on the gas connecting sleeve of a gas supply line, and does not need to be fastened by additional means.

For the uniform formation of bubbles it is advantageous that the inside diameter of the capillary tube increases at the nozzle and, in particular, is increased in a circular manner or, that the nozzle is expanded in a slit-like shape. In conjunction with this, it is beneficial that the difference between the inside and the outside diameters of the capillary tube at the outer end of the nozzle not be greater than 1 mm, and particularly not greater than 0.5 mm, and/or that the product of the thermal conductivity (W/K·m) and the wall thickness of the capillary tube at the outer end of the nozzle be smaller than $5.5 \times 10^{-3}$ W/K (Watt/Kelvin) at 1400° C. An arrangement of this type ensures the regular formation of bubbles that always exhibit a practically uniform diameter. It is also possible for the nozzle to be placed laterally on the capillary tube, by means of a lateral bore or a slit that is made (by means of sawing or milling, for example) in the capillary tube, for example.

It is advantageous, particularly for measurements in aggressive or very hot media, that the capillary tube be made of a gas-tight material, such as aluminum oxide, quartz, or zirconia, since these materials exhibit high temperature stability and are chemically resistant to many media, such as cast iron melts. For the accuracy and reproducibility of measurements it is beneficial that the connector be joined to the crucible in a gas-tight manner.

For a measurement device, the object is achieved by virtue of the fact that the connector is connected in a gas-tight manner to a gas connecting sleeve of a gas line and to a pressure sensor and/or flow meter, since the frequency of the gas bubbles that appear can be measured by using these devices.

BRIEF DESCRIPTION OF THE DRAWINGS

The foregoing summary, as well as the following detailed description of preferred embodiments of the invention, will be better understood when read in conjunction with the appended drawings which show further features and advantages of the invention. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF PREFERRED EMBODIMENT

Figure 1:
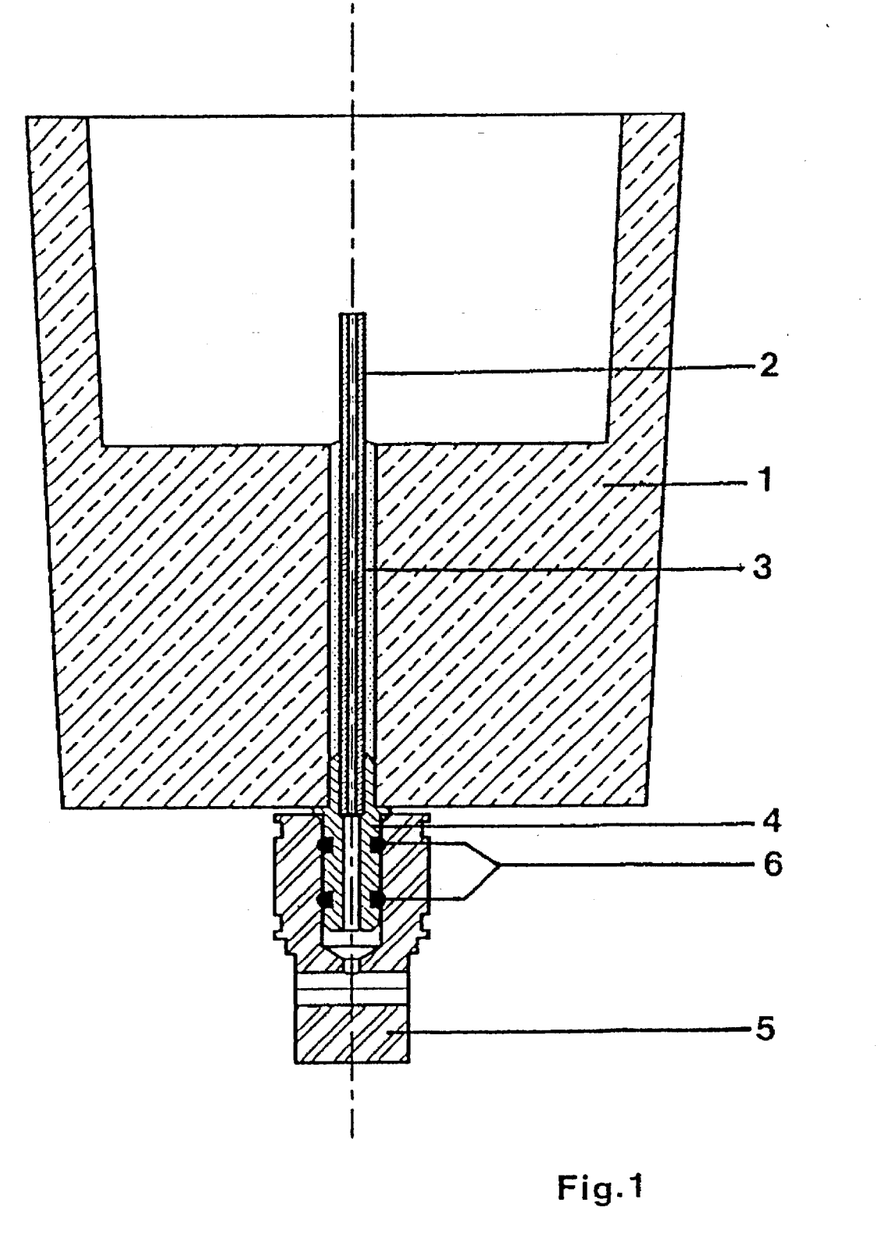
FIG. 1 is a sectional side view of a schematic representation of an apparatus in accordance with the invention, with arrangement of the capillary tube in the bottom of the crucible.

The crucible 1 shown in FIG. 1 is used for measurement of the surface tension of cast iron melts. However, it is also suitable for measurements of aluminum-silicon alloys or pig iron, for example. The crucible is made of a heat-resistant material, in the present case of resin-bonded sand or ceramic fibers. The bottom of the crucible 1 is made stronger (thicker) than the side walls in order to ensure the necessary stability of the crucible. The capillary tube 2 is run all the way through the bottom of the crucible and is fastened there by means of a refractory cement 3 in such a way as to prevent the melt from running out through the bottom of the crucible.

The capillary tube 2 is bonded to a connector 4, on which a gas connecting sleeve 5 is arranged. The connector 4 and the gas connecting sleeve 5 are used to supply gas to the capillary tube 2. The gas-tightness necessary for reproducibility of measurements is ensured by means of two O-rings 6, which are arranged between the connector 4 and the gas connecting sleeve 5. The crucible 1 is connected to the gas supply line and the measuring device by means of the gas connecting sleeve 5. The connector 4 and gas connecting sleeve 5 are made of metal, and the capillary tube 2 is made of a refractory material, such as aluminum oxide, zirconia, or quartz, for example. The capillary tube has an inside diameter of about 0.7–1.5 mm and projects to a height of about 5–25 mm into the interior hollow area of the crucible 1 that holds the melt.

The hollow area of the crucible 1 holds a melt volume of about 100 ml; smaller volumes can lead to a cooling of the melt, starting at the crucible wall, that progresses too quickly to allow an accurate measurement of the surface tension of the melt, after the melt is poured into the crucible 1, since a volume that is too small has a correspondingly low heat capacity and, therefore, cools off correspondingly quickly. To minimize the influence of this cooling effect on the measurement, the capillary tube 2 is arranged approximately on the axis of the rotationally symmetrical crucible 1, and the nozzle 7 is located about in the middle of the hollow area of the crucible 1.

Figure 2:
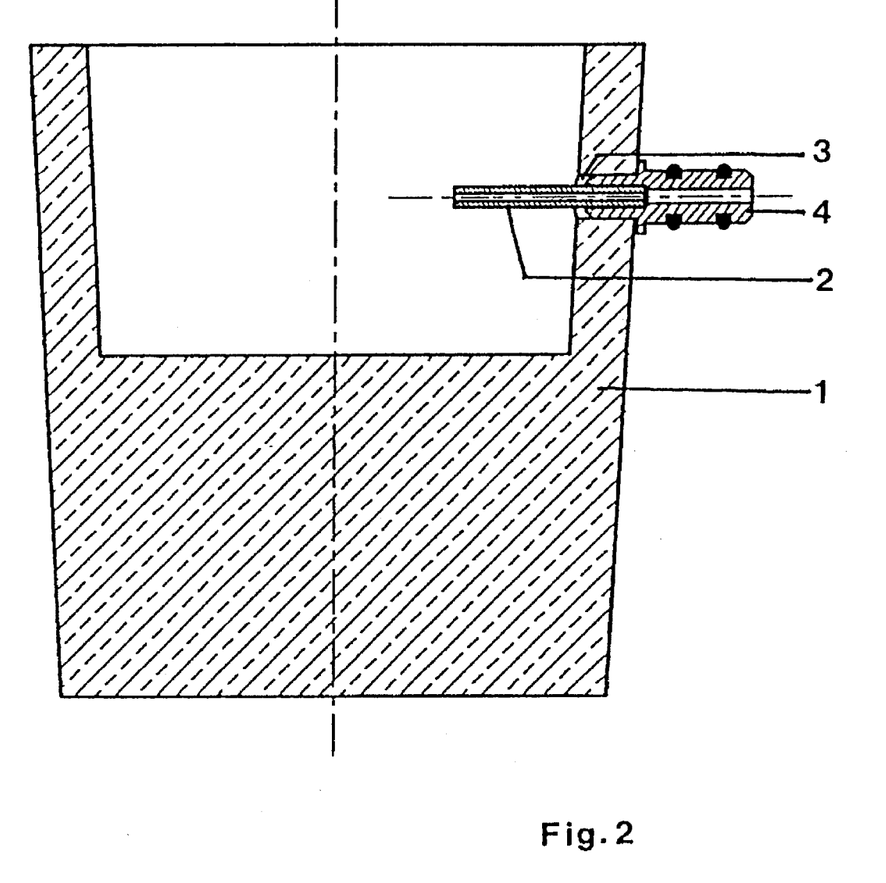
FIG. 2 is a sectional side view of a schematic representation of the apparatus with arrangement of the capillary tube in a side wall of the crucible.
Figure 3A:
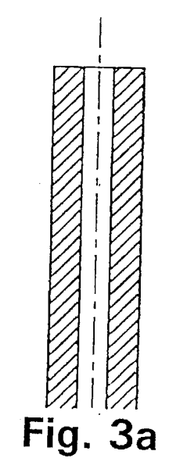
FIGS. 3a–h are longitudinal section views of several forms of nozzles for the capillary tube.
Figure 3B:
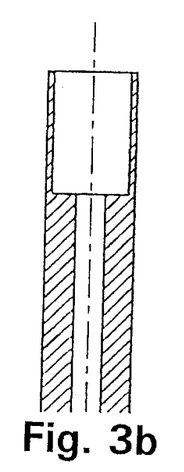
Figure 3C:
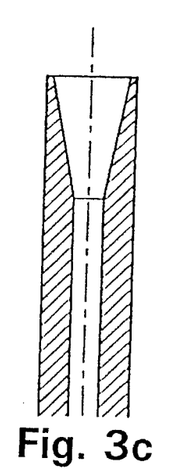
Figure 3D:
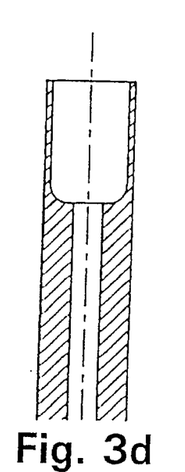
Figure 3E:
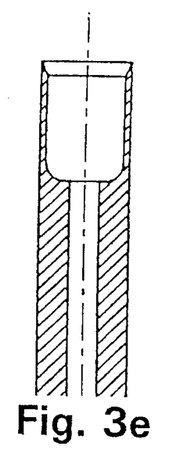
Figure 3F:
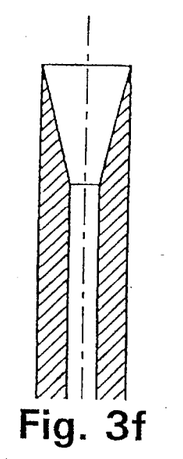
Figure 3G:
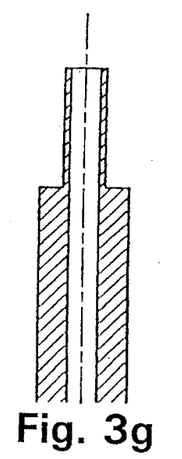
Figure 3H:
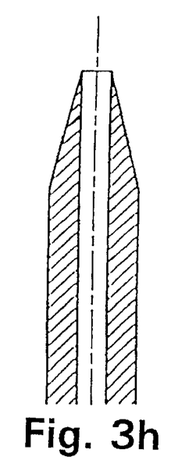

The crucible 1 shown in FIG. 2 is designed in a similar manner. The essential difference, with respect to the arrangement described above, resides in the arrangement of the capillary tube 2 in a side wall of the crucible 1.

FIG. 3 shows various nozzle forms for the capillary tube 2, as they can be used in the apparatus described at the beginning. What these nozzle forms have in common is that they are dimensioned in the apparatus in such a way that the difference between the outside and inside diameters of the capillary tube at the outer end of the nozzle amounts to 0.5 mm at most, so that the formation of gas bubbles of uniform size is assured. In this regard, it is conceivable to keep the inside diameter of the capillary tube constant over the entire length of the capillary tube, and to dimension the outside diameter at the outer end of the nozzle in an appropriate manner, as is shown in FIGS. 3a, g, and h. However, it is also conceivable to expand the inside diameter of the capillary tube at the nozzle in an appropriate manner. In this regard, the expansion can be carried out in the form of a cylindrical enlargement of the diameter, as shown in FIGS. 3b and d, or as a conical expansion in the direction of the outer end of the nozzle, as shown in FIGS. 3c and f. A combination of the two latter nozzle shapes is shown in FIG. 3e; here, the inside diameter of the capillary tube is expanded in a cylindrical fashion, and an additional, conical expansion is joined only at the outer end of the nozzle.

Figure 4:
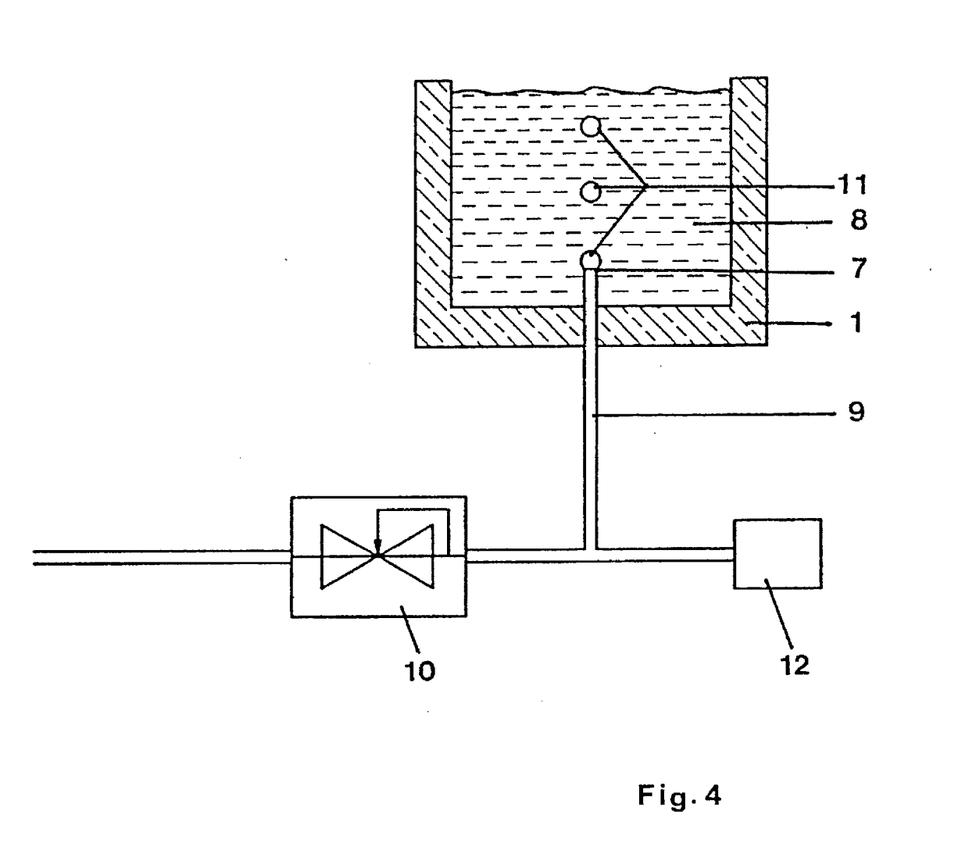
FIG. 4 is a schematic representation, partially in section, of a measuring device incorporating the apparatus of the invention.

A measuring device for the determination of surface tension is schematically shown in FIG. 4. The crucible 1 containing a cast iron melt 8 is connected to a gas line 9 through which the measurement gas is fed to the cast iron melt 8. The necessary gas flow is controlled by means of a gas flow regulating device 10 in the gas line 9. A gas that is inert with respect to the melt, such as argon or nitrogen, is used as the measurement gas that is blown into the cast iron melt 8 at about 2–15 ml per minute. The gas bubbles 11 are formed in the cast iron melt at the nozzle 7. In conjunction with this, a pressure that decreases abruptly following the release of the gas bubbles 11 from the nozzle 7 is built up in the gas line 9, and increases during the formation of a new gas bubble 11 until this bubble 11 releases.

Figure 5:
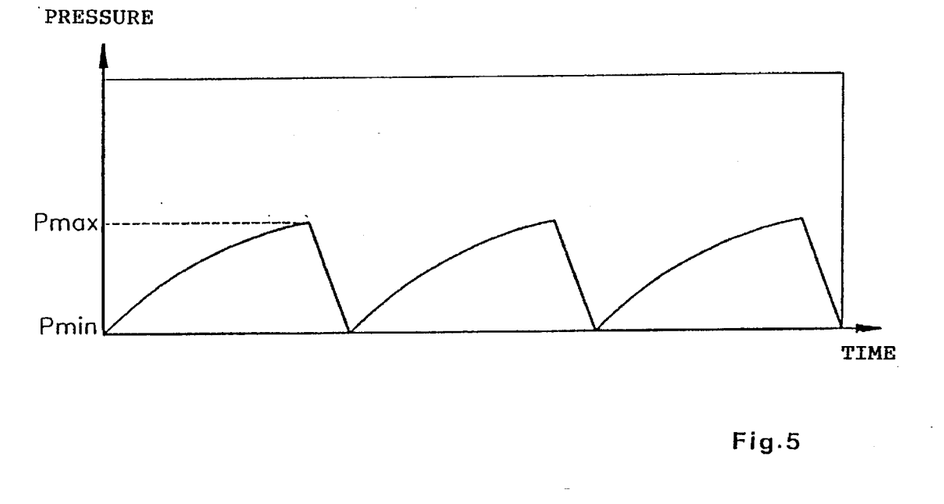
FIG. 5 is a pressure measurement curve for determination of the bubble frequency.

This pressure sequence, which is shown as a function of time in FIG. 5, is detected and recorded by a pressure sensor 12. The frequency of these pressure fluctuations brought about by the formation of the gas bubbles 11 is used for the calculation of the surface tension of the cast iron melt 8, or of a physical quantity that stands in a direct relationship with the surface tension, so that, as described at the beginning, the graphite morphology in the cast iron melt 8 can be determined. In this regard, the measurement time that is available for recording the pressure-time function is limited as a result of the solidification of the cast iron in the crucible 1. The available measurement time is determined by the difference between the pouring temperature of the cast iron melt 8 into the crucible 1 and the liquidus temperature of the cast iron, among other things. In order to monitor the temperature, a temperature sensor such as a thermocouple, for example, can be placed in the hollow area of the crucible 1.

Figure 6:
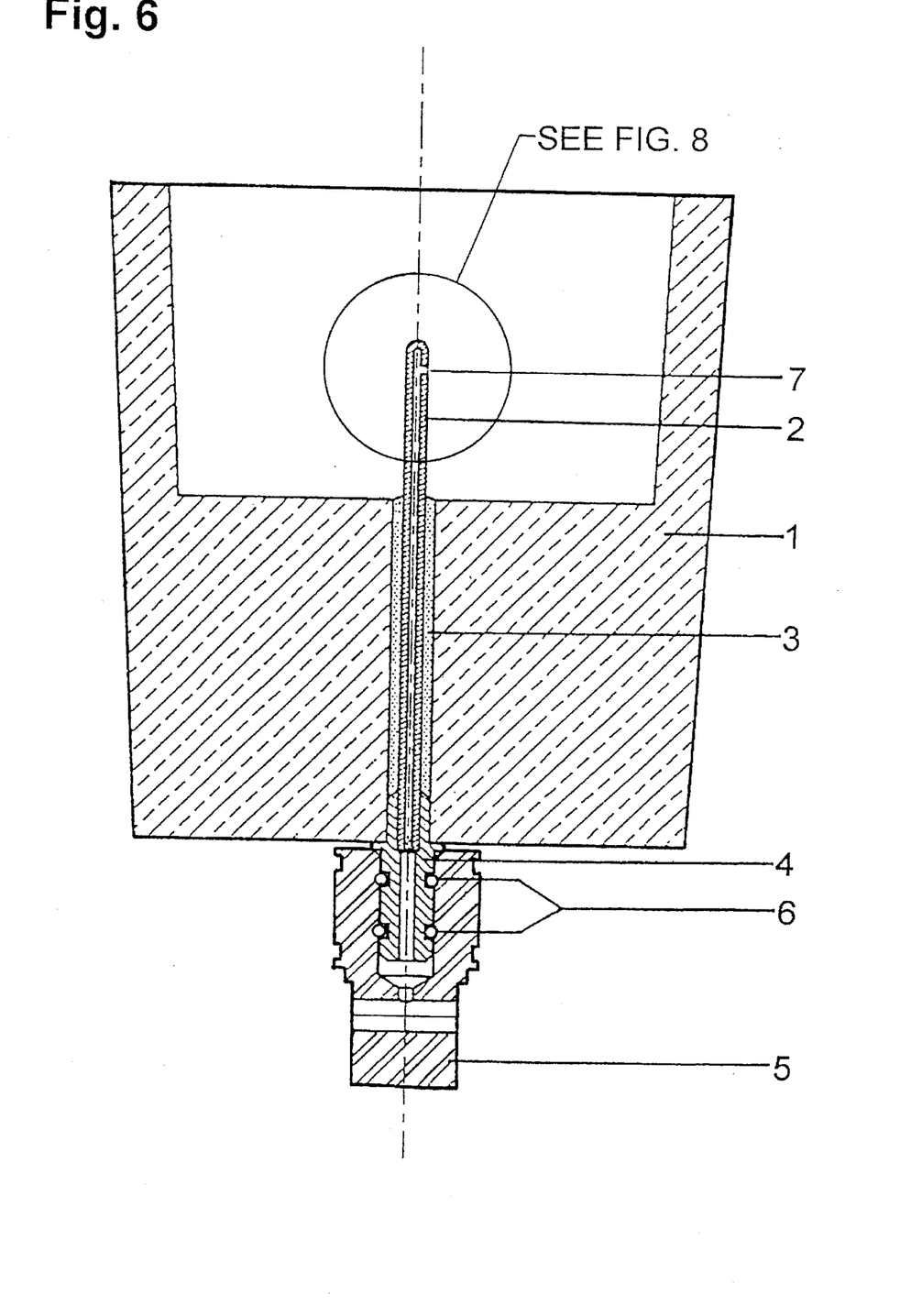
FIG. 6 is a sectional side view of a schematic representation of an apparatus similar to FIG. 1, but with the nozzle formed as a slit-like opening laterally on the capillary tube.
Figure 7:
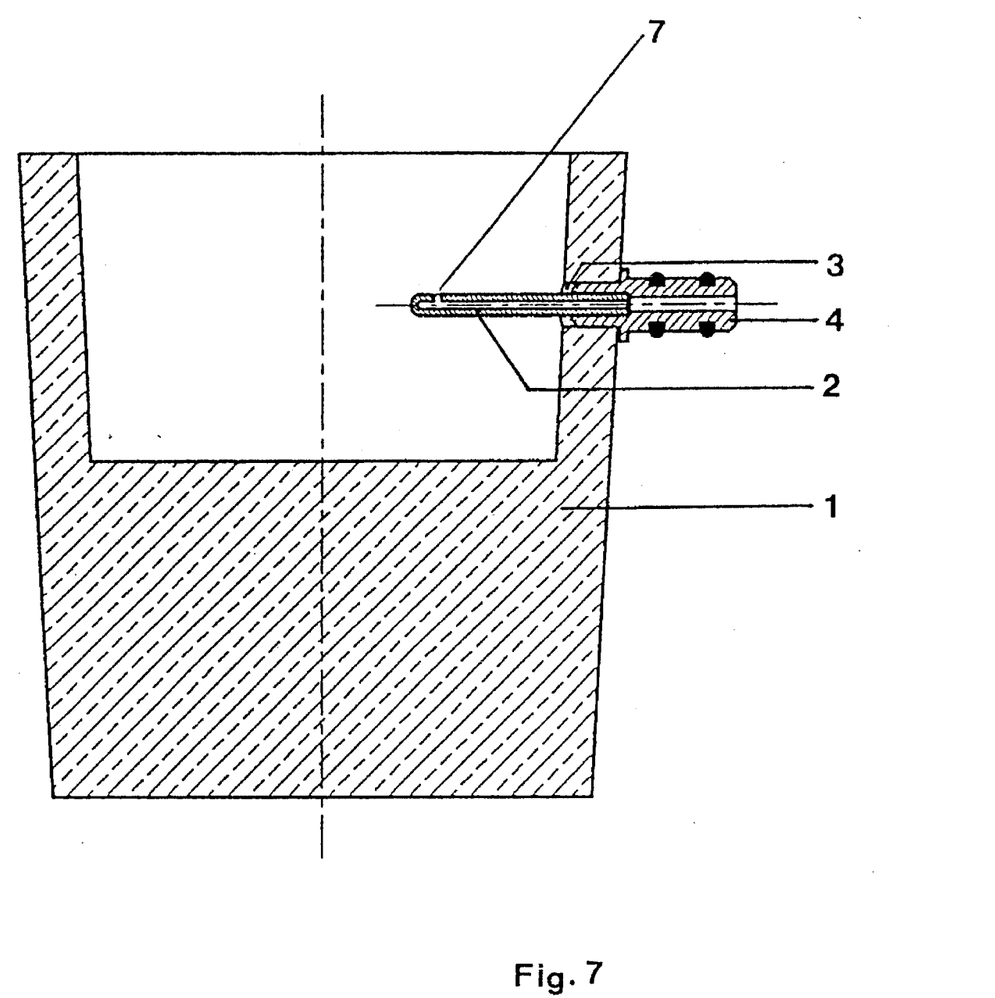
FIG. 7 is a sectional side view of a schematic representation of an apparatus similar to FIG. 2, but with the nozzle formed as a slit-like opening laterally on the capillary tube.

FIGS. 6 and 7 illustrate further preferred embodiments, similar to FIGS. 1 and 2, where the capillary tube 2 extends through the bottom or side wall, respectively, of the crucible. However, unlike FIGS. 1 and 2, where the capillary tube opening or nozzle is formed in the end of the tube, for example in one of the forms shown in FIG. 3, the nozzle 7 in FIGS. 6 and 7 is in the form of a circumferential slit or slit-like opening in the lateral wall of the capillary tube, preferably near its end inside the crucible and remote from the crucible bottom or side wall. This slit may suitably be formed by sawing or milling the tube in a radial or near radial direction, preferably perpendicular to the longitudinal axis of the tube. In the case of side wall mounting, the slit preferably faces upward to ensure free release and uniform bubble formation.

Figure 8:
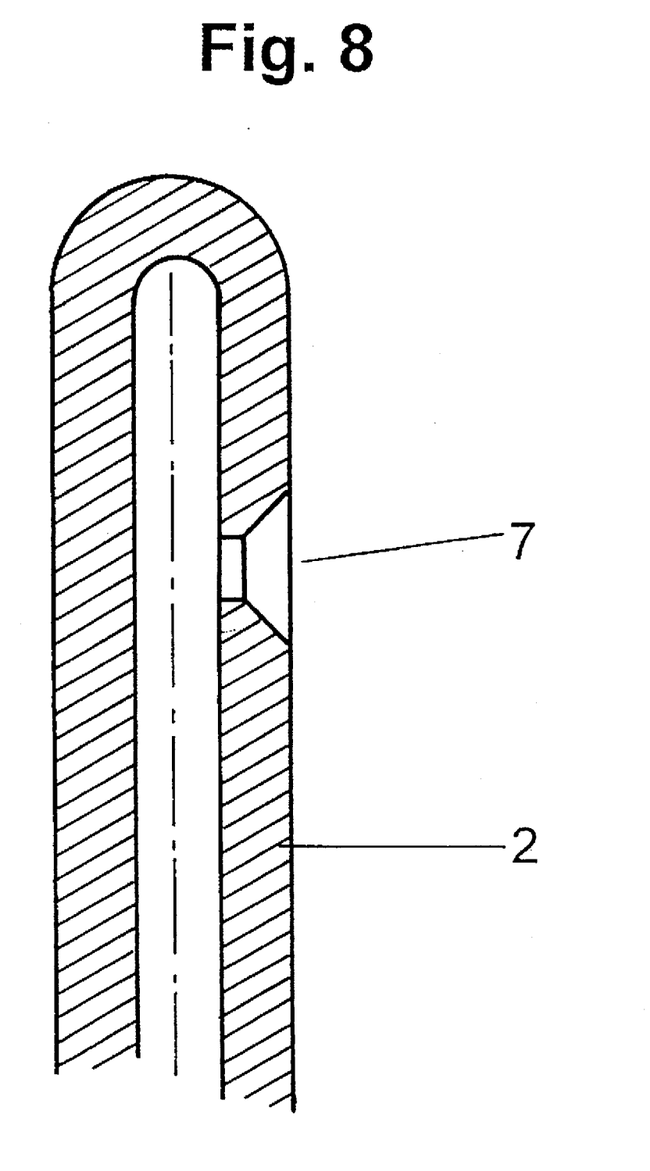
FIG. 8 is an enlarged view taken from FIG. 6 showing an alternative nozzle formed on a lateral side of the capillary tube.

FIG. 8 illustrates another alternative embodiment of the capillary tube 2 having the nozzle 7 located on the side of the capillary tube 2. The nozzle 7 has a diameter which increases at the nozzle end.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. An apparatus for measuring the surface tension of liquids, comprising a capillary tube for supplying a gas, the capillary tube (2) having a connector and a nozzle, and being arranged, at least partially, in a crucible (1) for holding a liquid, the crucible having bottom and side walls, the tube being mounted on a selected one of the bottom and side walls of the crucible (1) and running through the selected one of the bottom and side walls of the crucible (1), and the connector (4) being arranged outside an interior of the crucible (1), and being configured as a crucible mounting, and the nozzle (7) being configured with a slit-like shape.

2. The apparatus according to claim 1, wherein the capillary tube (2) runs through the bottom of the crucible (1).

3. The apparatus according to claim 1, wherein the difference between an inner and an outer diameter of the capillary tube (2) at an end of the nozzle (7) is not greater than 1 mm.

4. The apparatus according to claim 3, wherein the difference is not greater than 0.5 mm.

5. The apparatus according to claim 1, wherein the product of thermal conductivity and wall thickness of the capillary tube at an end of the nozzle is smaller than $5.5 \times 10^{-3}$ W/K at 1400° C.

6. The apparatus according to claim 1, wherein the capillary tube (2) comprises a gas-tight material.

7. The apparatus according to claim 6, wherein the gas-tight material is selected from the group consisting of aluminum oxide, quartz, and zirconia.

8. A measuring device comprising a gas line and an apparatus according to claim 1, wherein the connector (4) is connected in a gas-tight manner to a gas connecting sleeve (5) of the gas line (9) and to at least one of a pressure sensor (12) and a flow meter.

9. An apparatus for measuring the surface tension of liquids, comprising a capillary tube for supplying a gas, the capillary tube (2) having a connector and a nozzle with an opening, and being arranged, at least partially, in a crucible (1) for holding a liquid, the tube being mounted to and extending through the crucible (1) and running through a wall of the crucible (1), the connector (4) being arranged outside an interior of the crucible (1), being mounted to the bottom of the crucible (1), and the nozzle (7) being located on a lateral side of the capillary tube (2) and having a diameter which increases at the nozzle opening.

* * * * *